United States Patent
Goll (12) 
(10) Patent No.: US 6,344,027 B1
(45) Date of Patent: Feb. 5, 2002

(54) NEEDLE-LESS INJECTION APPARATUS AND METHOD

(75) Inventor: J. Paul Goll, Woodinville, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/456,456

(22) Filed: Dec. 8, 1999

(51) Int. Cl.⁷ .................................................. A61M 5/30

(52) U.S. Cl. .......................................... 604/68; 604/69

(58) Field of Search .............................. 604/68, 69, 70, 604/71, 72, 131, 140, 141, 143, 147

(56) References Cited

U.S. PATENT DOCUMENTS

| | | | |
|---|---|---|---|
| 4,578,061 A | 3/1986 | Lemelson | 604/164 |
| 4,596,556 A | 6/1986 | Morrow et al. | 604/70 |
| 4,790,824 A | 12/1988 | Morrow et al. | 604/143 |
| 4,964,853 A | * 10/1990 | Sugiyama et al. | 604/96 |
| 5,064,413 A | 11/1991 | McKinnon et al. | 604/70 |
| 5,098,389 A | 3/1992 | Cappucci | 604/158 |
| 5,236,424 A | 8/1993 | Imran | 604/280 |
| 5,262,128 A | 11/1993 | Leighton et al. | 422/100 |
| 5,324,276 A | 6/1994 | Rosenberg | 604/269 |
| 5,354,279 A | 10/1994 | Hofling | 604/164 |
| 5,383,851 A | 1/1995 | McKinnon, Jr. et al. | 604/68 |
| 5,385,548 A | * 1/1995 | Williams et al. | 604/96 |
| 5,399,163 A | 3/1995 | Peterson et al. | 604/68 |
| 5,403,311 A | 4/1995 | Abele et al. | 606/49 |
| 5,419,777 A | 5/1995 | Hofling | 604/264 |
| 5,457,041 A | 10/1995 | Ginaven et al. | 435/172.1 |
| 5,464,395 A | 11/1995 | Faxon et al. | 604/96 |
| 5,472,441 A | 12/1995 | Edwards et al. | 606/41 |
| 5,478,328 A | 12/1995 | Silverman et al. | 604/272 |
| 5,520,639 A | 5/1996 | Peterson et al. | 604/68 |
| 5,538,504 A | 7/1996 | Linden et al. | 604/53 |
| 5,672,174 A | 9/1997 | Gough et al. | 606/41 |
| 5,693,029 A | 12/1997 | Leonhardt | 604/264 |
| 5,697,901 A | 12/1997 | Eriksson | 604/46 |
| 5,702,384 A | 12/1997 | Umeyama et al. | 604/892.1 |
| 5,766,164 A | 6/1998 | Mueller et al. | 606/15 |
| 5,782,823 A | 7/1998 | Mueller | 606/7 |
| 5,807,395 A | 9/1998 | Mulier et al. | 606/41 |

(List continued on next page.)

FOREIGN PATENT DOCUMENTS

| | | |
|---|---|---|
| CA | 2241615 | 12/1998 |
| DE | 196 07 922 A1 | 9/1997 |
| EP | 0 934 728 A2 | 8/1999 |
| WO | WO 92/10142 | 6/1992 |
| WO | WO 92/10142 A1 | 6/1992 |
| WO | WO 98/05307 A1 | 2/1998 |
| WO | WO 99/04851 | 2/1999 |
| WO | WO 99/39624 A1 | 8/1999 |
| WO | WO 99/44524 | 9/1999 |
| WO | WO 99/48545 A1 | 9/1999 |
| WO | WO 99/49926 | 10/1999 |

OTHER PUBLICATIONS

Internet Article, 'Taking the "Ouch" Out of Needles: Arrays of Micron–Scale "Microneedles" Offer New Technique For Drug Delivery', John Toon, Released Jun. 22, 1998, 4 pp.
"Chemical Engineers Develop Microneedles for Painfree Injections," Dec. 1998, one page, source unknown.

*Primary Examiner*—Manual Mendez
(74) *Attorney, Agent, or Firm*—Kenyon & Kenyon (57) ABSTRACT

A device and method for delivering and injecting fluid into heart tissue utilizing high pressure injection to increase injectate (fluid) retention in the heart tissue. The catheter includes a shaft having an infusion lumen extending therethrough, wherein the proximal end of the shaft connected to a pressurized fluid source capable of generating a transient pressure of more than 1000 psi. The distal end of the shaft includes a nozzle having an injection port in fluid communication with the infusion lumen such that fluid from the pressurized fluid source may be delivered to the heart tissue at a sufficiently high exit velocity to partially penetrate the heart tissue.

18 Claims, 4 Drawing Sheets

U.S. PATENT DOCUMENTS

| | | | |
|---|---|---|---|
| 5,830,222 A | 11/1998 | Makower | 606/159 |
| 5,840,061 A | 11/1998 | Menne et al. | 604/68 |
| 5,843,017 A | 12/1998 | Yoon | 604/22 |
| 5,882,332 A | 3/1999 | Wijay | 604/53 |
| 5,997,525 A | 12/1999 | March et al. | 604/508 |
| 6,063,082 A | 5/2000 | DeVore et al. | 606/45 |
| 6,093,185 A | 7/2000 | Ellis et al. | 606/28 |
| 6,203,556 B1 | 3/2001 | Evans et al. | 606/185 |

\* cited by examiner

NEEDLE-LESS INJECTION APPARATUS AND METHOD

RELATED APPLICATIONS

This application is related to co-pending patent application Ser. No. 09/457,453, filed on even date herewith, entitled INJECTION ARRAY APPARATUS AND METHOD, co-pending patent application Ser. No. 09/457,254, filed on even date herewith, entitled LATERAL NEEDLE INJECTION APPARATUS AND METHOD, and co-pending patent application Ser. No. 09/457,193, filed on even date herewith, entitled LATERAL NEEDLE-LESS INJECTION APPARATUS AND METHOD.

FIELD OF THE INVENTION

The present invention generally relates to delivering and injecting fluid into heart tissue. More specifically, the present invention relates to delivering and injecting fluid into heart tissue utilizing needle-less injection.

BACKGROUND OF THE INVENTION

Injection catheters may be used to inject therapeutic or diagnostic agents into a variety of organs, such as the heart. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters. One limitation to this method of delivering therapeutic agents to the heart is that the injected fluid tends to leak from the site of the injection after the needle is disengaged from the heart. In fact, fluid may continue to leak over several seconds. In the case of dynamic organs such as the heart, there may be more pronounced leakage with each muscle contraction. A second limitation to this method is that the injected fluid remains as a bolus at the injection site and is not distributed over a very wide area. A third limitation is that needles leave more permanent trauma.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guide wire and a balloon catheter. In these procedures, a balloon catheter is advanced over a guide wire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesion are not practical, percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency or laser energy delivered by a catheter having one or more electrodes near its distal end. After the wound has been created, therapeutic agents are sometimes injected into the heart chamber from the distal end of a catheter.

Positive clinical results have been demonstrated in human patients receiving PMR treatments. These results are believed to be caused, in part, by blood flowing within the heart chamber through channels in myocardial tissue formed by PMR. Increased blood flow to the myocardium is also believed to be caused, in part, by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes injected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

Currently available injection catheters are not particularly suitable for accurately delivering small volumes of therapeutic agents to heart tissue. Improved devices and methods are desired to address the problems associated with retention of the agent in the heart tissue as discussed above. This is particularly true for agents carrying genes, proteins, or other angiogenic drugs which may be very expensive, even in small doses.

SUMMARY OF THE INVENTION

The present invention provides an improved apparatus and method for delivering and injecting fluid into heart tissue. The present invention addresses the problems associated with retention of the fluid in the heart tissue and disbursement of the fluid throughout a wider tissue area by utilizing high pressure needle-less injection. The present invention may be used to deliver genes, proteins or drugs directly into the myocardium for purposes of myocardial revascularization. The present invention provides an improved apparatus and method for causing transient trauma that may stimulate angiogenesis.

In an exemplary embodiment, the present invention provides a catheter system including an injection catheter connected to a pressurized fluid source capable of generating a high transient pressure sufficient to pierce tissue. The injection catheter includes an elongate shaft defining an infusion lumen in fluid communication with the fluid contained in the pressurized fluid source. The distal end of the shaft includes a nozzle having an injection port in fluid communication with the infusion lumen such that fluid from the pressurized fluid source may be delivered to the heart tissue at a sufficiently high exit velocity to partially penetrate the heart tissue.

To accommodate the relatively high pressures involved, the shaft of the injection catheter may be formed of a metal or a reinforced polymer composite to withstand the pressure burst. The injection port may have a small diameter in the range of 0.001 to 0.05 inches, depending on the desired injection parameters, such as exit velocity, volume delivered, target tissue area, etc. The injection port may be larger or smaller than the lumen in the nozzle in order to change the exit velocity adjacent the port. In addition, the nozzle may be sharpened in order to partially penetrate the heart tissue.

The present invention also provides a method of delivering a fluid to heart tissue including the steps of: providing a pressurized fluid source and an injection catheter substantially as described above; inserting the injection catheter into the patient; navigating the catheter until the distal end of the catheter is positioned adjacent the injection site; and actuating the fluid source to inject fluid into the heart tissue via the infusion lumen of the shaft and the injection port at a sufficient exit velocity to partially penetrate the heart tissue.

By utilizing high pressure needle-less injection, the present invention reduces trauma as compared to needle based systems. In addition, the high pressure needle-less injection system of the present invention reduces fluid leakage from the injection site and distributes injected fluid over a greater volume of tissue.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1A:
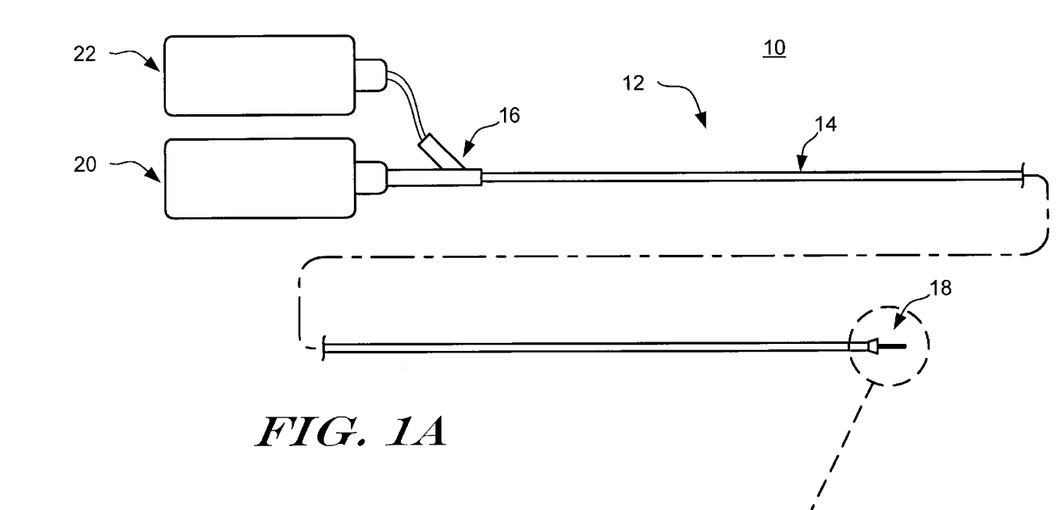
FIG. 1A is a plan view of a catheter system in accordance with an exemplary embodiment of the present invention.

Refer to FIG. 1A which illustrates a plan view of a catheter system 10 in accordance with an exemplary embodiment of the present invention. Catheter system 10 includes a catheter assembly 12 having an elongate catheter shaft 14. A manifold 16 is connected to the proximal end of the elongate shaft 14. The catheter assembly 12 includes an outer sheath 28 and an inner injection catheter 24, each of which include elongate shafts collectively referred to as elongate shaft 14. The elongate shaft 14 includes a distal portion 18 which is illustrated in greater detail in FIG. 1B.

The elongate shaft 14 has characteristics (length, profile, flexibility, pushability, trackability, etc.) suitable for navigation from a remote access site to the treatment site within the human body. For example, the elongate shaft 14 may have characteristics suitable for intravascular navigation to the coronary tissue from a remote access site in the femoral artery. Alternatively, the elongate shaft 14 may have characteristics suitable for transthoracic navigation to the coronary tissue from a remote access point in the upper thorax. Those skilled in the art will recognize that the shaft 14 may have a wide variety of dimensions, materials, constructions, etc., depending on the particular anatomy being navigated.

A pressurized fluid source 20 is connected to the catheter 12 by way of the manifold 16. Optionally, a vacuum source 22 may be coupled to the side arm of the manifold 16. Vacuum source 22 may comprise a conventional syringe or other suitable vacuum means such as a vacuum bottle. The pressurized fluid source 20 may comprise a variety of high pressure injection systems. For example, the pressurized fluid source 20 may comprise a conventional syringe having a small diameter plunger and barrel coupled to a mechanical or pneumatic means to actuate the plunger relative to the barrel in order to generate high pressures. Preferably, an automated high pressure injection system is utilized as disclosed in U.S. Pat. No. 5,520,639 to Peterson et al., U.S. Pat. No. 5,399,163 to Peterson et al., U.S. Pat. No. 5,383,851 McKinnon et al., U.S. Pat. No. 5,064,413 to McKinnon et al., U.S. Pat. No. 4,790,824 to Morrow et al., or U.S. Pat. No. 4,596,556 to Morrow et al. each of which are hereby incorporated by reference.

The needle-less injection devices disclosed in the aforementioned patents in addition to the needle-less injection device commercially available from Bioject, Inc. are transdermal injection devices that may be readily modified to be used as pressurized fluid source 20 in the present invention. Specifically, in each of the transdermal injection devices, the nozzle used to create and direct the fluid stream through the skin may be replaced with a means to fluidly couple the device to the manifold 16. Alternatively, the nozzle may be retained and directly coupled to the manifold 16.

The pressurized fluid source 20 preferably generates a pressure of approximately 5000 psi (peak) or more in less than 1 second in order to pierce the tissue at the treatment site. The pressurized fluid source 20 may generate a pressure in the range of 4000–7000 psi, and may be coupled to pressure and flow regulators to control the pressure and volume of fluid delivered through the catheter 12. The pressure range may be modified depending on the tissue characteristics, but must be sufficiently high to pierce the tissue. The pressurized fluid source 20 preferably has a relatively low internal volume in order to minimize fluid waste after the desired amount of fluid has been delivered to the tissue. The internal fluid volume of the pressurized fluid source may range from 10 μl to 1.0 ml, but preferably has the ability to deliver less than 100 μl of fluid.

Figure 1B:
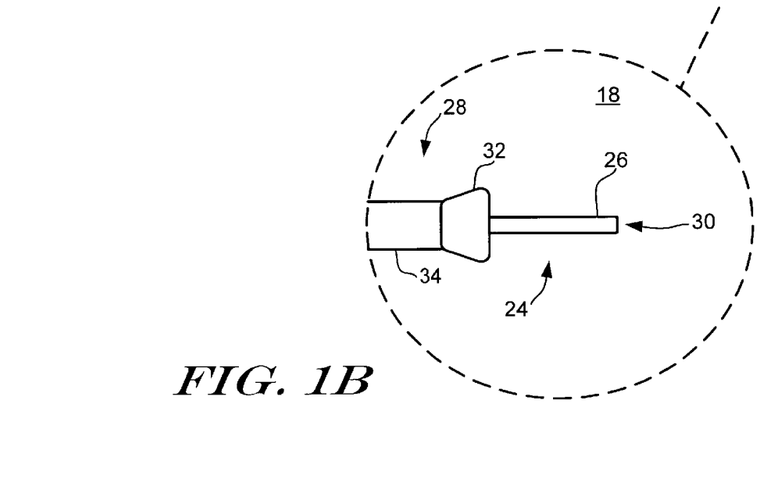
FIG. 1B is an enlarged detailed view of the distal end of the catheter illustrated in FIG. 1A.
Figure 2:
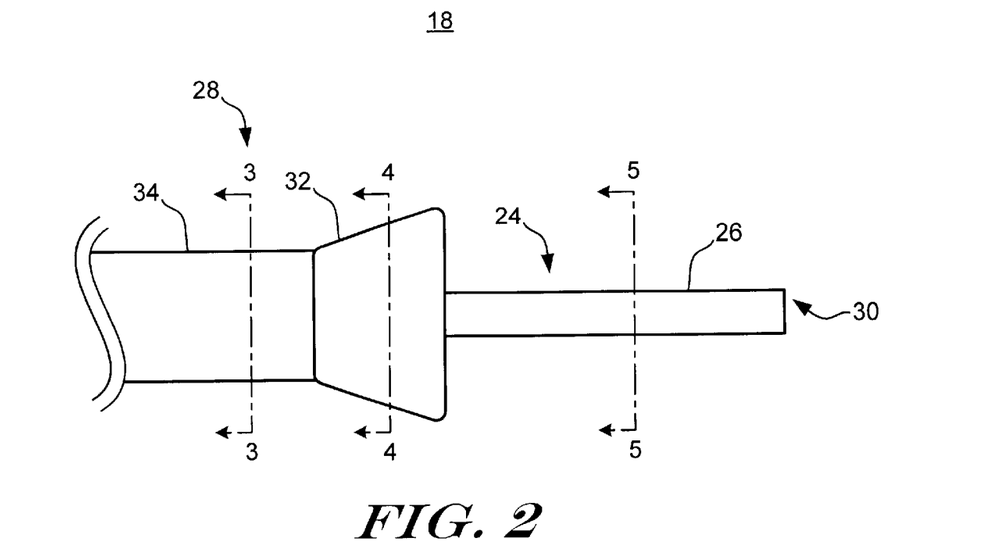
FIG. 2 is a further enlarged view of the distal end of the catheter illustrated in FIG. 1A.

Refer now to FIG. 1B which illustrates an enlarged detailed view of the distal portion 18 of the elongate shaft 14. Elongate shaft 14 includes an injection catheter 24 coaxially disposed in an elongate outer sheath 28. A nozzle 26 is disposed adjacent the distal end of the injection catheter 24. The nozzle 26 may be a separate component connected to the distal end of the injection catheter 24, or an integral part of the injection catheter 24. In either embodiment, the nozzle 26 defines an injection port 30. Various embodiments of the nozzle 26 and the injection port 30 are discussed in more detail with reference to FIGS. 6A–6E. The injection port 30 is in fluid communication with the pressurized fluid source 20 via the nozzle 26, the injection catheter 24 and the manifold 16.

The outer sheath 28 includes an elongate shaft 34 with a suction head 32 connected to the distal end of the shaft 34. To increase the contact surface area with the tissue, the suction head 32 may have a generally conical shape as shown. The suction head 32 is preferably made of a soft polymeric material to reduce tissue trauma and to increase conformity with the tissue surface in order to create a fluid seal therebetween for suction and stabilization purposes discussed hereinafter.

Refer now to FIGS. 2–5 which illustrate the distal portion 18 and various cross-sectional views thereof. With specific reference to FIG. 2, the injection catheter 24 includes a nozzle 26 defining a port 30. Nozzle 26 may be blunt or sharpened, depending on whether the injection port 30 is to be disposed adjacent to the heart tissue or partially penetrate the heart tissue. The injection port 30 may face distally as illustrated or may face laterally, depending on the configuration of the nozzle 26. The arrangement and size of the injection port 30 determines, in part, the various injection parameters as will be discussed in greater detail with reference to FIGS. 6A–6E.

Figure 3:
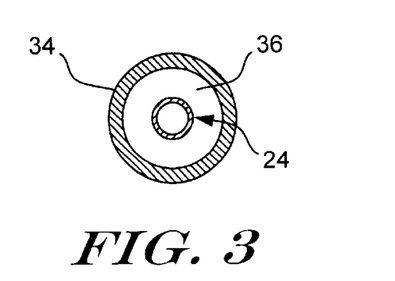
FIG. 3 is a lateral cross-sectional view taken along line 3—3 in FIG. 2.

With specific reference to FIG. 3, the injection catheter 24 is coaxially disposed in the outer sheath 28 to define an annular lumen 36. The annular lumen 36 may be used to infuse fluids for purposes of fluoroscopic visualization and/ or aspiration. Alternatively, the annular lumen 36 may be used to facilitate the application of suction for stabilization purposes. For the application of suction, the inner lumen 36 of the outer sheath 28 is in fluid communication with the vacuum source 22. By actuating the vacuum source 22, suction is applied to the suction head 32 via the inner lumen 36. When the suction head 32 is positioned adjacent the heart tissue, the suction head 32 grasps the surface of the heart tissue thereby stabilizing the distal portion 18 of the catheter assembly 12.

Figure 4:
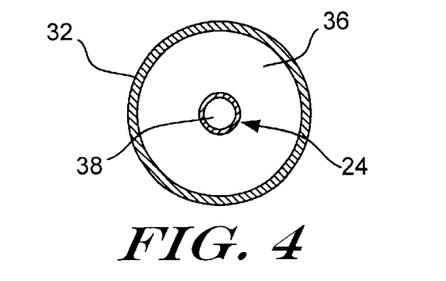
FIG. 4 is a lateral cross-sectional view taken along line 4—4 in FIG. 2.
Figure 5:
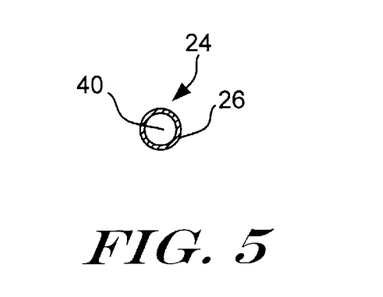
FIG. 5 is a lateral cross-sectional view taken along line 5—5 in FIG. 2.

With reference now to FIGS. 4 and 5, nozzle 26 includes a nozzle lumen 40 in fluid communication with the infusion lumen 38. Infusion lumen 38 is in fluid communication with the injection port 30 via nozzle lumen 40. Thus, injection port 30 is in fluid communication with the pressurized fluid source 20 via lumen 38 such that fluid may be readily delivered from the pressurized fluid source 20, through the shaft of the injection catheter 24, through the nozzle 26, through the injection port 30 and into the heart tissue. Fluid communication between the pressurized fluid source 20 and the injection port 26 may be defined by direct connection between the proximal end of the injection catheter 24 or by an intennediate tube connected to the proximal end of the injection catheter 24.

The injection catheter 24 is preferably formed of a metal tube or a reinforced polymer composite tube to withstand transient pressures in excess of 4000 psi. For example, the injection catheter 24, or a substantial portion thereof, may be formed of a metal such as stainless steel or a super elastic alloy such as nickel titanium. Alternatively, the injection catheter 24, or a substantial portion thereof, may be formed of a metal reinforced polymer composite such as a polymer tube with an embedded stainless steel braid. Preferably, to accommodate the necessary flexibility of the distal end, the proximal portion of the injection catheter 24 may be formed of a metal such as stainless steel or nickel titanium, and the distal portion may be formed of a metal reinforced polymer composite. Those skilled in the art will recognize that a wide variety of materials and constructions may be utilized to create injection catheter 24, as long as the materials and constructions are selected to withstand transient pressures in excess of 4000 psi. The inside diameter of the injection catheter 24 should be sufficiently large to accommodate the desired flow rate of fluid, but sufficiently small to reduce the amount of fluid waste remaining in the lumen 38 after the procedure is complete. For example, the injection catheter 24 may have an inside diameter in the range of 0.002 to 0.10 inches.

Refer now to FIGS. 6A–6E which illustrate various embodiments of the nozzle 26 disposed adjacent the distal end of the injection catheter 24. As mentioned previously, the nozzle 26 may be formed as an integral part of the injection catheter 24, or may be formed as a separate piece and connected to the distal end of the injection catheter 24. Preferably, the nozzle 26 is formed of a relatively rigid material that resists radial expansion when exposed to transient pressures in excess of 4000 psi.

Figure 6A:
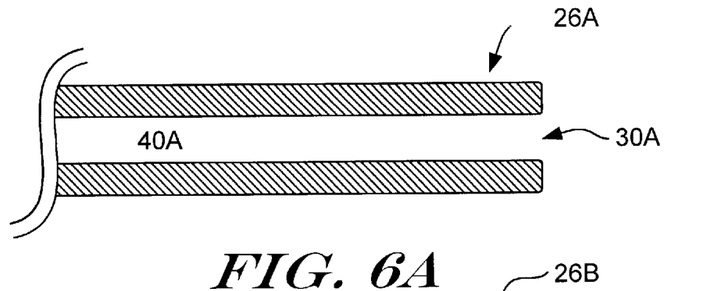
FIGS. 6A–6E illustrate various embodiments of the distal end of the injection member.
Figure 6B:
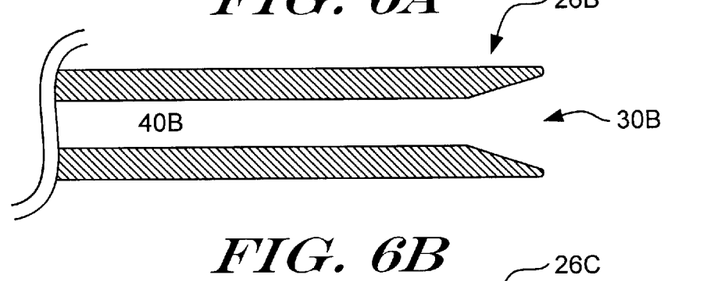

As mentioned previously, nozzle 26 includes a nozzle lumen 40 in fluid communication with the infusion lumen 38 of the injection catheter 24. The nozzle lumen 40 may have a constant diameter or may be varied along its length to create various fluid flow conditions. For example, the nozzle lumen 40A may have substantially the same diameter as injection port 30A as illustrated in FIG. 6A. Alternatively, the injection port 30B may have a diameter larger than the diameter of the nozzle lumen 40B as shown in FIG. 6B, such that fluid exiting the injection port 30B decreases in pressure and velocity, but increases in area. Alternatively, the injection port 30C may have a diameter smaller than the diameter of the nozzle lumen 40C as shown in FIG. 6C, such that the fluid exiting the injection port 30C increases in pressure and velocity, but decreases in area.

Figure 6C:
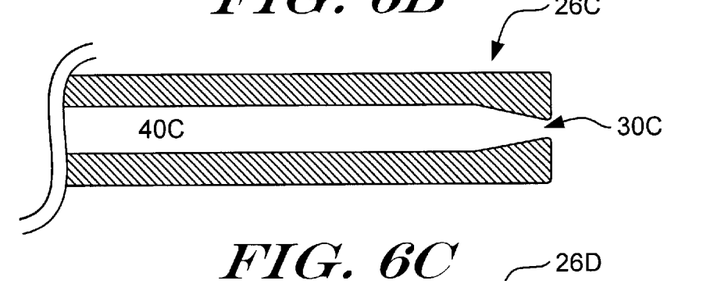
Figure 6D:
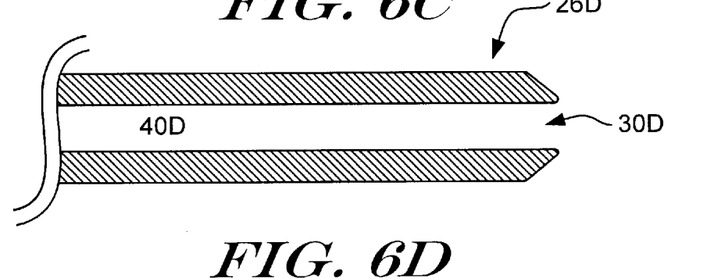
Figure 6E:
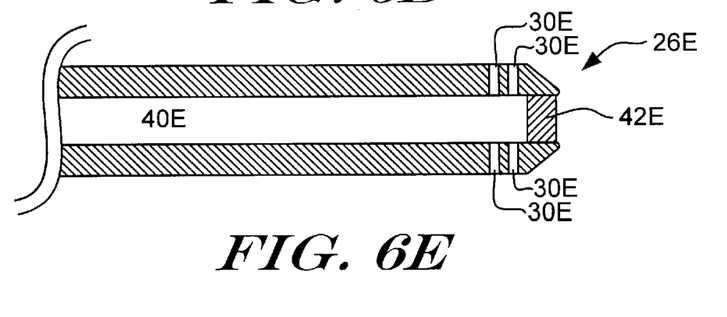

The distal end of the nozzle 26 may be blunt as illustrated in FIGS. 6A–6C or may be sharpened as illustrated in FIG. 6D. The sharpened distal end of the nozzle 26D facilitates insertion of the distal end thereof partially into the heart tissue. In particular, the sharpened end of the nozzle 26D facilitates insertion of the injection port 30C just below the epicardial or endocardial surface of the heart, depending on the approach. The injection port 30C may face distally as shown in FIG. 6D or may face latterly as shown in FIG. 6E. A plug 42E may be disposed in the distal end of the nozzle lumen 40E such that fluid exits the lateral injection ports 30E only. Once the sharpened end of the nozzle 26E penetrates the epicardial or endocardial surface of heart, the injection port(s) 30D/30E is/are positioned in the epicardial or endocardial space to deliver fluid therein.

The penetration depth of the fluid exiting the injection port 30 into the heart tissue influences tissue trauma, fluid retention in the tissue, and the volume of tissue treated with the fluid. The penetration depth of the fluid is dictated, in part, by the exit velocity of the fluid from the injection port 30, nature of the fluid, the size of the fluid stream exiting the injection port 30, and the properties of the heart tissue (i.e., the myocardium, epicardium, endocardium). The exit velocity, in turn, depends on the applied pressure of the pressurized fluid source 20, the drag or pressure drop along the length of the infusion lumen 38 and nozzle lumen 40, and the cross-sectional area or size of the injection port 30. The size of the fluid stream exiting the injection port 30 also depends on the size and geometry of the nozzle 26, and in particular, the size and geometry of the nozzle lumen 40 and injection port 30. Thus, assuming the treatment site dictates the tissue properties, and the particular therapy dictates the fluid and thus the fluid properties, the penetration depth may be selected by adjusting the applied pressure of the pressurized fluid source 20, the size and length of the infusion lumen 38, and the size and geometry of the nozzle 26 (i.e., the nozzle lumen 40 and injection port 30). By adjusting these parameters, fluid retension, treated tissue volume and degree of tissue trauma may be modified as required for the particular clinical application.

Figure 7A:
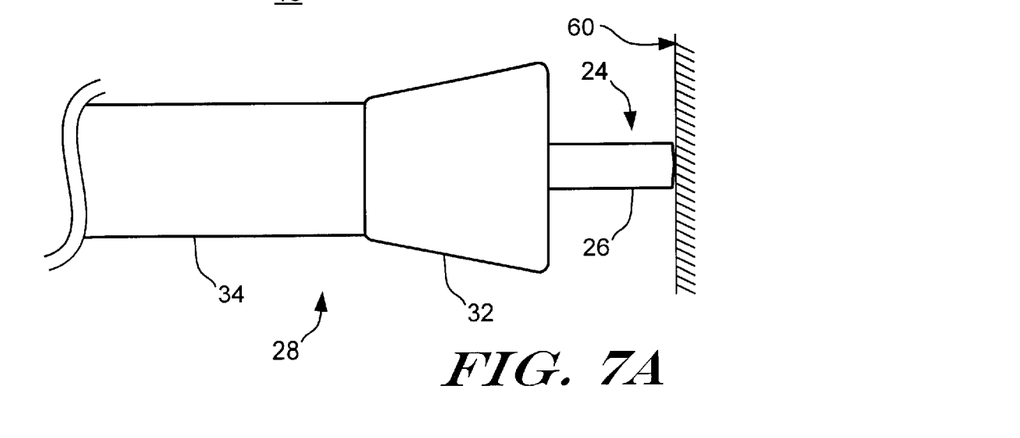
FIGS. 7A–7C illustrate a sequence of steps for using the system illustrated in FIG. 1A.
Figure 7B:
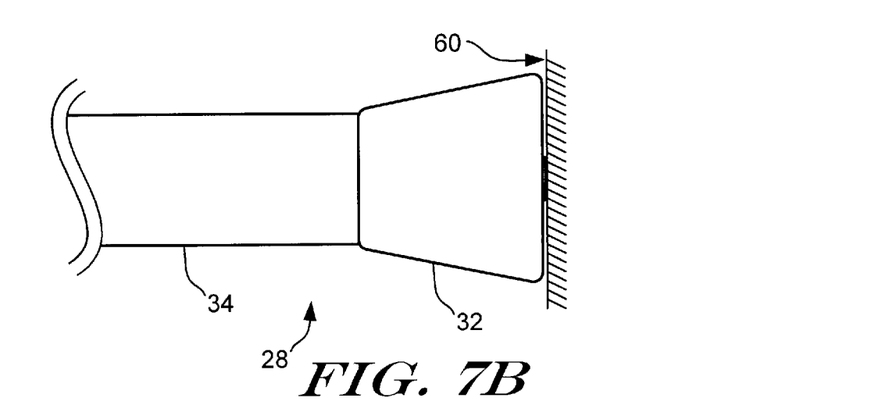
Figure 7C:
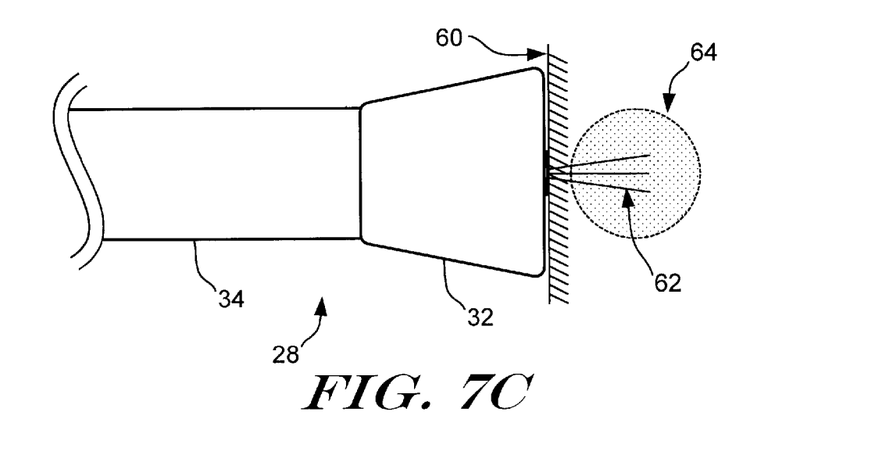

Refer now to FIGS. 7A–7C which illustrate operation of the catheter system 10. The heart tissue 60 (i.e., epicardium, myocardium and/or endocardium) may be accessed from the interior of the heart by, for example, navigating the catheter 12 through the vascular system into a chamber of the heart adjacent the endocardium. Alternatively, the heart tissue 60 may be accessed from the exterior of the heart by, for example, transthoracic minimumly invasive surgery in which the catheter 12 is navigated through the upper thoracic cavity adjacent the epicardium of the heart.

Regardless of the approach, the distal portion 18 of the catheter 12 is positioned adjacent the desired treatment site of the heart tissue 60 utilizing conventional visualization techniques such as x-ray fluoroscopy or endoscopic visualization. While positioning the catheter 12, the injection catheter 24 may be partially retracted in the outer sheath 28 such that the distal end of the injection catheter 24 is exposed, or fully retracted such that the entire injection catheter 24 is contained within the outer sheath 28.

With the distal portion 18 positioned adjacent the heart tissue 60 as shown in FIG. 6A, the injection catheter 24 is advanced adjacent the surface of the heart tissue 60. If the tip of the nozzle 26 is blunt as illustrated in FIGS. 6A–6C, the distal end of the injection catheter 24 is positioned adjacent to the heart tissue 60. If the distal tip of the nozzle 26 is sharpened as illustrated in FIGS. 6D and 6E, the distal end of the injection catheter 24 is advanced a sufficient depth to position the injection port 26 just below the epicardial or endocardial surface. This position may be confirmed by injecting radiopaque contrast media or colored dye through the inner lumen 38 of the injection catheter 34 such that the contrast media or dye exits the injection port 26 adjacent the desired treatment site.

If the optional suction head 32 is incorporated onto the shaft 34 of the outer sheath 28, the outer sheath 28 is advanced until the distal end of the suction head 32 is disposed adjacent the surface of the heart tissue 60. The suction head 32 grasps the surface of the heart tissue 60 upon application of a vacuum by the vacuum source 22. By grasping the surface of the heart tissue 60, the suction head 32 stabilizes the distal portion 18 of the catheter 12. This is particularly beneficial when treating tissue in a dynamic situation such as when the heart is beating. Absent a stabilizing means such as suction head 32, it may be difficult to maintain the distal portion 18 in a relatively fixed position relative to the heart tissue 60. Those skilled in the art will recognize that other stabilizing means may be utilized such as removable screw anchors, miniature forceps, etc.

Once the outer sheath 28 and the injection catheter 24 are in the desired position, fluid 62 may be delivered from the pressurized fluid source 20 through the lumen 38 of the injection catheter 24, through the lumen 40 of the nozzle 26 and out the injection port 26 and into the heart tissue 60. After the fluid 62 has been delivered via the injection port 26, the injection catheter 24 may be retracted into the outer sheath 28. After retraction, the entire catheter 12 may be removed from the patient.

As can be appreciated from the illustration of FIG. 6C, by injecting the fluid 62 utilizing the high pressure needle-less system 10 of the present invention, the fluid 62 is distributed over a greater volume 64 of heart tissue 60 without causing as much trauma as would occur with a needle-based injection system. Specifically, the injected fluid stream 62 is exposed to the heart tissue 60 along the entire length of the stream 62. By providing more contact between the tissue 60 and the fluid stream 62, a greater volume 64 of tissue is treated thereby retaining more fluid with less permanent trauma than would otherwise be achieved with a needle-based system.

From the foregoing, it is apparent that the present invention provides a device and method for delivering and injecting fluid into heart tissue to improve fluid retention and reduce permanent trauma. This is accomplished by utilizing a high pressure needle-less injection system including an injection catheter capable of withstanding pressure bursts in excess of 1000 psi.

Although treatment of the heart is used as an example herein, the medical devices of the present invention are useful for treating any mammalian tissue or organ. Non-limiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone.

The terms "therapeutic agents" and "drugs" are used interchangeably herein and include pharmaceutically active compounds, cells, nucleic acids with and without carrier vectors such as lipids, compacting agents (such as histones), virus, polymers, proteins, and the like, with or without targeting sequences.

Specific examples of therapeutic agents used in conjunction with the present invention include, for example, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/ anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidominc, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), an d the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The present invention is also useful in delivering cells as the therapeutic agent. Cells can be of human origin (autologous or allogeneic) or from an animal source (xenogeneic), genetically engineered if desired to deliver proteins of interest at a delivery or transplant site. The delivery media is formulated as needed to maintain cell function and viability.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A catheter system for delivering a fluid to heart tissue, comprising:
   a pressurized fluid source containing a fluid therein, the pressurized fluid source generating a high transient pressure sufficient to pierce bodily tissue; and
   an injection catheter including an elongate shaft having a proximal end, a distal end and an infusion lumen extending therein, the proximal end of the shaft connected to the pressurized fluid source, the infusion lumen in fluid communication with the fluid contained in the pressurized fluid source, the distal end of the shaft including a nozzle having an injection port in fluid communication with the infusion lumen such that fluid from the pressurized fluid source may be delivered to the heart tissue via the infusion lumen of the shaft and the injection port at a sufficient exit velocity to partially penetrate the heart tissue.

2. A catheter system as in claim 1, wherein the shaft of the injection catheter is formed of a metal to withstand the high transient pressure.

3. A catheter system as in claim 2, wherein the shaft of the injection catheter is formed of stainless steel along a substantial length thereof.

4. A catheter system as in claim 2, wherein the shaft of the injection catheter is formed of a super elastic alloy along a substantial length thereof.

5. A catheter system as in claim 1, wherein the shaft of the injection catheter is formed of a metal reinforced polymer composite to withstand the high transient pressure.

6. A catheter system as in claim 5, wherein the shaft of the injection catheter is formed of a stainless steel reinforced polymer along a substantial length thereof.

7. A catheter system as in claim 5, wherein the shaft of the injection catheter is formed of a super elastic alloy reinforced polymer along a substantial length thereof.

8. A catheter system as in claim 1, wherein the injection port has a diameter of 0.05 inches or less.

9. A catheter system as in claim 1, wherein the injection port has a diameter of 0.010 inches or less.

10. A catheter system as in claim 1, wherein the injection port has a diameter of 0.005 inches or less.

11. A catheter system as in claim 1, wherein the nozzle defines a nozzle lumen having a diameter, and wherein the injection port has a diameter substantially the same as the diameter of the nozzle lumen.

12. A catheter system as in claim 1, wherein the nozzle defines a nozzle lumen having a diameter, and wherein the injection port has a diameter smaller than the diameter of the nozzle lumen to increase the exit velocity of the fluid.

13. A catheter system as in claim 1, wherein the nozzle defines a nozzle lumen having a diameter, and wherein the injection port has a diameter larger than the diameter of the nozzle lumen to decrease the exit velocity of the fluid.

14. A catheter system as in claim 1, wherein the nozzle includes a sharpened distal end to partially penetrate the heart tissue.

15. A catheter system as in claim 1, wherein the injection port is directed distally.

16. A catheter system as in claim 1, wherein the injection port is directed laterally.

17. A catheter system as in claim 1, further comprising:
 a vacuum source; and
 a sheath disposed about the injection catheter, the sheath having a proximal end, a distal end and a suction lumen disposed therein, the proximal end of the sheath connected to the vacuum source with the suction lumen of the sheath in fluid communication with the vacuum source, wherein the distal end of the sheath is disposed adjacent the heart tissue such that the distal end of the sheath is stabilized against the heart tissue when a vacuum is applied to the suction lumen using the vacuum source.

18. A method of delivering a fluid to an injection site in heart tissue of a patient, comprising the steps of:
 providing a pressurized fluid source containing a fluid therein, the pressurized fluid source generating a high transient pressure sufficient to pierce bodily tissue;
 providing an injection catheter comprising a shaft having a proximal end, a distal end and an infusion lumen extending therein, the distal end of the catheter including a nozzle and an injection port;
 inserting the injection catheter into the patient;
 navigating the catheter until the distal end of the catheter is positioned adjacent the injection site; and
 actuating the fluid source to inject fluid into the heart tissue via the infusion lumen of the shaft and the injection port at a sufficient exit velocity to partially penetrate the heart tissue.

\* \* \* \* \*